(12) United States Patent
Chadeayne

(10) Patent No.: US 12,006,290 B2
(45) Date of Patent: Jun. 11, 2024

(54) CRYSTALLINE NORPSILOCIN COMPOUNDS

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 17/906,575

(22) PCT Filed: Mar. 18, 2021

(86) PCT No.: PCT/US2021/022992
§ 371 (c)(1),
(2) Date: Sep. 16, 2022

(87) PCT Pub. No.: WO2021/188812
PCT Pub. Date: Sep. 23, 2021

(65) Prior Publication Data
US 2023/0112410 A1 Apr. 13, 2023

Related U.S. Application Data

(60) Provisional application No. 62/991,912, filed on Mar. 19, 2020.

(51) Int. Cl.
| | |
|---|---|
| *A61K 31/675* | (2006.01) |
| *A61K 31/01* | (2006.01) |
| *A61K 31/4045* | (2006.01) |
| *A61K 45/06* | (2006.01) |
| *C07C 57/15* | (2006.01) |
| *C07D 209/16* | (2006.01) |

(52) U.S. Cl.
CPC ............ *C07D 209/16* (2013.01); *A61K 31/01* (2013.01); *A61K 31/4045* (2013.01); *A61K 31/675* (2013.01); *A61K 45/06* (2013.01); *C07C 57/15* (2013.01); *C07B 2200/13* (2013.01)

(58) Field of Classification Search
CPC .................................................. A61K 31/675
See application file for complete search history.

(56) References Cited

U.S. PATENT DOCUMENTS

| | | | |
|---|---|---|---|
| 2009/0209539 A1 | 8/2009 | Leblanc et al. | |
| 2018/0021326 A1 | 1/2018 | Stamets | |
| 2018/0221396 A1* | 8/2018 | Chadeayne | .......... A61K 31/675 |
| 2019/0142851 A1 | 5/2019 | Chadeayne | |
| 2021/0069170 A1 | 3/2021 | Stamets | |

OTHER PUBLICATIONS

Chadeayne et al., Research Communication, 2020, E76: 589-593.*
Aixala, M., Dos Santos, R. G., Hallak, J. E. C. & Bouso, J. c. (2018). ACS Chem. Neurosci. 9, 2304-2306.
Bradley, R. J. & Johnston, V. S. (1970). Origin and Mechanism of Hallucinations, edited by W. Keup, pp. 333-344. New York: Plenum Press.
Cameron, L. P., Benson, C. J., DeFelice, B. C., Fiehn, 0. & Olson, D. E. (2019). ACS Chem. Neurosci. In the press. http://doi.org/10.1021/acschemneuro.8b00692.
Cameron, L. P. & Olson, D. E. (2018). ACS Chem. Neurosci. 9, 2344-2357.
Carhart-Harris, R. L. & Goodwin, G. M. (2017). Neuropsychopharmacology, 42, 2105-2113.
Dinis-Oliveira, R. J. (2017). Drug Metab. Rev. 49, 84-91.
Dolomanov, O. V., Bourhis, L. J., Gildea, R. J., Howard, J. A. K. & Puschmann, H. (2009). J. Appl. Cryst. 42, 339-341.
Fontanilla, D., Johannessen, M., Hajipour, A. R., Cozzi, N. V., Jackson, M. B. & Ruoho, A. E. (2009). Science, 323, 934-937.
J. Gartz, Int. J. Crude Drug Res., 1989, 27, 141-144.
N. Jensen, J. Gartz and H. Laatsch, Planta Med., 2006, 72, 665-666.
Johnson, M. W. & Griffiths, R.R. (2017). Neurotherapeutics 14, 734-740.
Lenz, C., Wick, J. & Hoffmeister, D. (2017). J. Nat. Prod. 80, 2835-2838.
Leung, A. Y. & Paul, A.G. (1968). J. Pharm. Sci. 57, 1667-1671.
Nichols, D. E. (2012). WIREs Membr. Transp. Signal. 1, 559-579.
Nichols, D. E. (2016). Pharmacol. Rev. 68, 264-355.
Passie, T., Seifert, J., Schneider, U. & Emrich, H. M. (2002). Addict. Biol. 7, 357-364.
Russo, E. B. (2011). Br. J. Pharmacol. 163, 1344-1364.
Sheldrick, G. M. (2015a). Acta Cryst. A71, 3-8.
Sheldrick, G. M. (2015b). Acta Cryst. C71, 3-8.
Sherwood, A. M., Halberstadt, A. L., Klein, A. K., McCorvy, J. D., Kaylo, K. W., Kargbo, R. B. & Meisenheimer, P. (2020). J. Nat. Prod. 83, 461-467.

(Continued)

*Primary Examiner* — Rei Tsang Shiao
(74) *Attorney, Agent, or Firm* — RAPHAEL BELLUM PLLC

(57) ABSTRACT

The disclosure relates to norpsilocin compounds, compositions containing those crystalline compounds, and methods of treatment using them. The norpsilocin compounds include crystalline 4-hydroxy-N-methyltryptamine ("crystalline 4-HO-NMT" or "crystalline norpsilocin freebase"), crystalline 4-hydroxy-N-methyltryptammonium fumarate ("crystalline norpsilocin fumarate"), and 4-hydroxy-N-methyltryptammonium fumarate ("norpsilocin fumarate") and their compositions and uses.

11 Claims, 7 Drawing Sheets

(56) References Cited

OTHER PUBLICATIONS

Stamets, P. (1996). Psilocybin mushrooms of the world: An identification guide. Berkeley, CA: Ten Speed Press.
Westrip, S. P. (2010). J. Appl. Cryst. 43, 920-925.
Zhuk, 0., Jasicka-Misiak, I., Poliwoda, A., Kazakova, A., Godovan, V. V., Halama, M. & Wieczorek, P. (2015). Toxins, 7, 1018-1029.
International Preliminary Report on Patentability of PCT International Application No. PCT/US2021/022992, dated Sep. 20, 2022.
International Search Report and Written Opinion in International Application No. PCT/US2021/022992 dated May 3, 2021.
Chadeayne et al., "Norpsilocin: freebase and fumarate salt", Crystallographic Communications, Mar. 2020, pp. 589-593.
Carlson et al., "An integrated high throughput workflow for pre-formulations: Polymorph and salt selection studies", Pharm. Chem, Drug Development, pp. 10-15, Jul./Aug. 2003.

* cited by examiner

CRYSTALLINE NORPSILOCIN COMPOUNDS

CROSS-REFERENCE TO RELATED APPLICATIONS

This application claims priority to U.S. Provisional Application No. 62/991,912 filed on Mar. 19, 2020.

TECHNICAL FIELD

This disclosure relates to norpsilocin compounds, compositions, and pharmaceutical compositions containing them as well as their use in treating various diseases. The norpsilocin compounds according to the disclosure including crystalline 4-hydroxy-N-methyltryptamine ("crystalline 4-HO-NMT" or "crystalline norpsilocin freebase"), crystalline 4-hydroxy-N-methyltryptammonium fumarate ("crystalline norpsilocin fumarate"), and 4-hydroxy-N-methyltryptammonium fumarate ("norpsilocin fumarate").

BACKGROUND

The focus of psychedelics in therapy has largely been on psilocybin and psilocin. Despite the focus on these two compounds, there are more than 200 species of "magic mushrooms" containing many different psychoactive tryptamines and combinations of the same (Stamets, 1996). The clinical effects observed for extracts of "magic mushrooms" differ from those observed from pure psilocybin (Zhuk, et al. 2015). This indicates that the minor components of "magic mushrooms" have psychoactive properties that are important, or that they work in conjugation with psilocybin as part of an entourage effect (Russo, 2011). To have a better understanding of "magic mushroom" pharmacology, and to optimize the clinical experience of tryptamine-based psychedelics, it is important to understand the properties of the minor active components.

N,N-dimethyltryptamine (DMT) and its derivatives have been used by humans for centuries because of their psychoactive, entheogenic, or hallucinogenic effects, or combinations thereof (Cameron & Olson, 2018). Psilocybin, the 4-phosphate variant of DMT, is arguably its most studied derivative. Psilocybin is one of several naturally occurring psychoactive tryptamines found in "magic mushrooms." When consumed by humans, psilocybin serves as a prodrug of psilocin. Upon digestion, psilocybin hydrolyses to generate psilocin, the 4-hydroxy derivative of DMT. Psilocin is a potent serotonin 2a-agonist, which is responsible for its psychoactive properties (Dinis-Oliveira, 2017; Nichols, 2012).

Baeocystin, the monomethyl analog of psilocybin, is the second most abundant naturally occurring tryptamine found in "magic mushrooms." It was first isolated from the mushroom Psilocybe baeocystin in 1968 (Leung & Paul, 1986), and subsequently identified in other species as up to about one third of the total tryptamine concentration. Like psilocybin, baeocystin acts as a prodrug when consumed by humans, undergoing rapid hydrolysis of the phosphate ester to afford its active metabolite—the 4-hydroxy analog.

The prodrug psilocybin hydrolyses to the active 4-hydroxy-N,N-dimethyltryptamine (4-HO-DMT), aka psilocin, and the prodrug baeocystin hydrolyses to the active 4-hydroxy-N-methyltyrptamine (4-HO-NMT), aka norpsilocin. Norpsilocin was first identified as a natural product of "magic mushrooms" in 2017, and isolated as an amorphous, colorless solid (Lenz, et al. 2017). In 2020, norpsilocin was synthesized and when tested as an agonist at the human serotonin 2a receptor, synthetic norpsilocin was as potent if not more compared to psilocin (Sherwood, et al. 2020).

N-methyl-N-propyltryptamine (MPT) is a structural analog of N,N-dimethyltryptamine (DMT), which is a well-known 'psychedelic' molecule found in a variety of naturally occurring organisms, including plants, animals, and fungi, including mushrooms. In humans, DMT is the only known endogenous mammalian N,N-dimethylated trace amine (Fontanilla et al., 2009). Naturally occurring tryptamines (e.g. DMT, psilocybin, 5-methoxy-N,N-dimethyltryptamine) and their synthetic derivatives (e.g. psilacetin, MPT) have garnered considerable attention of late due to new evidence demonstrating their efficacy in treating mood (e.g. anxiety and depression) and post-traumatic stress disorders (PTSDs) (Aixalà et al., 2018; Cameron et al., 2019).

Psilocybin, isolated from the so-called "magic mushrooms," is perhaps the best-known prodrug of the serotonin 2a agonist psilocin (Nichols, 2016). Psychoactive tryptamines like DMT and psilocin show the potential for treating mood disorders, including depression, anxiety, addiction, and post-traumatic stress disorder (PTSD) (Johnson & Griffiths, 2017; Carhart-Harris & Goodwin, 2017). However, the long duration of action of psilocin and its prodrugs can result in practical challenges for both patients and clinicians (Passie et al., 2002). Accordingly, the mental health industry would benefit from exploring alternative tryptamine treatment options that provide similar therapeutic benefits while having a shorter duration of action.

Altering the chemical structure within this class of compounds can dramatically influence the potency and action of the drugs. For example, merely changing the N,N-dialkyl groups on DMT can modify its psychoactive properties: increasing the chain length of the two alkyl groups of the tryptamine to larger than n-butyl dramatically reduces or eliminates the psychoactive effects (Bradley & Johnston, 1970).

New psychoactive tryptamines have been identified in "magic mushrooms" as recently as 2017. (Lentz, et al., 2017.) Until this year, there was no general synthetic method for producing useful amounts of the minor psychoactive tryptamines. (Sherwood, Halberstadt, et al.) One of these minor components is aeruginascin, (Jensen, et al., 2006) the N-trimethyl analogue of psilocybin. The limited exposure of humans to *Inocybe aeruginascens* mushrooms, the only known species in which aeruginascin has been found, has resulted in hallucinations that exhibited only euphoric experiences. (Gartz, 1989). This is in contrast to psilocybin and psilocin mushrooms, which often lead to dysphoric moods during the psychedelic experience. Despite these observations, the pharmacological activity of aeruginascin has remained unexplored.

Even with this previous work, there is a need to develop new psilocybin derivatives with improved properties for treatment of psychological disorders.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to norpsilocin compounds and to pharmaceutical compositions containing them. The norpsilocin compounds according to the disclosure include crystalline 4-hydroxy-N-methyltryptamine ("crystalline 4-HO-NMT" or "crystalline norpsilocin freebase"), crystalline 4-hydroxy-N-methyltryptammonium fumarate ("crystalline norpsilocin fumarate"), and 4-hydroxy-N-methyltryptammonium fumarate ("norpsilocin fumarate").

The disclosure relates to compositions comprising crystalline norpsilocin freebase, crystalline norpsilocin fumarate, or norpsilocin fumarate and an excipient. The disclosure also relates to pharmaceutical compositions comprising a therapeutically effective amount of crystalline norpsilocin freebase, crystalline norpsilocin fumarate, or norpsilocin fumarate, where the excipient is a pharmaceutically acceptable carrier. The disclosure further relates to a method of preventing or treating a psychological disorder comprising the step of administering to a subject in need thereof a therapeutically effective amount of crystalline norpsilocin freebase, crystalline norpsilocin fumarate, or norpsilocin fumarate, or of a pharmaceutical composition containing the compounds.

The disclosure also relates to a composition comprising as a first active component: crystalline norpsilocin freebase, crystalline norpsilocin fumarate, or norpsilocin fumarate of the disclosure; and as a second active component selected from (a) a serotonergic drug, (b) a purified psilocybin derivative, (c) one or two purified cannabinoids and (d) a purified terpene; and a pharmaceutically acceptable excipient.

The disclosure further relates to methods of preventing or treating a physical and/or psychological disorders comprising the step of administering to a subject in need thereof an effective amount of crystalline norpsilocin freebase, crystalline norpsilocin fumarate, or norpsilocin fumarate, or a composition according to the disclosure.

The disclosure also relates to methods of preventing or treating inflammation and/or pain comprising the step of administering to a subject in need thereof a therapeutically effective amount of crystalline norpsilocin freebase, crystalline norpsilocin fumarate, or norpsilocin fumarate, and to administering a pharmaceutical composition or a composition according to the disclosure.

In one embodiment, crystalline norpsilocin freebase according to the disclosure is characterized by a monoclinic, $P2_1/c$ crystal system space group at a temperature of about 297 K; unit cell dimensions a=9.4060 (16) Å, b=8.8436 (15) Å, c=12.144 (2) Å, and β=100.601 (7)°; or an XRPD having peaks at 9.6, 12.4, and 17.9°2θ±0.2°2θ.

In one embodiment, crystalline norpsilocin fumarate according to the disclosure is characterized by a triclinic, P$\bar{1}$ crystal system space group at a temperature of about 297 K; unit cell dimensions a=7.7363 (10) Å, b=9.7146 (12) Å, c=9.7854 (13) Å, α=105.524 (4)°, β=110.554 (4)°, and γ=97.167 (4)°; or an XRPD having peaks at 11.5, 13.9, and 16.2°2θ±0.2° 2θ.

DETAILED DESCRIPTION

Figure 1:
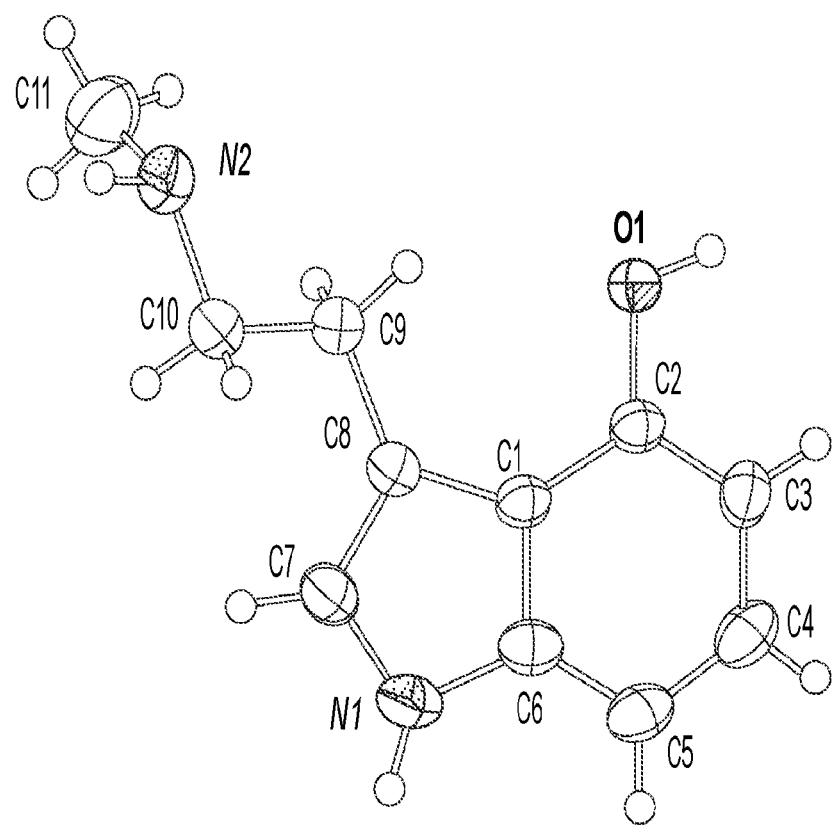
FIG. 1 shows the molecular structure of crystalline norpsilocin freebase.

The disclosure relates to norpsilocin compounds and to pharmaceutical compositions containing them. The norpsilocin compounds according to the disclosure include crystalline 4-hydroxy-N-methyltryptamine ("crystalline 4-HO-NMT" or "crystalline norpsilocin freebase"), crystalline 4-hydroxy-N-methyltryptammonium fumarate ("crystalline norpsilocin fumarate"), and 4-hydroxy-N-methyltryptammonium fumarate ("norpsilocin fumarate"). The therapeutic uses of the norpsilocin compounds according to the disclosure, are described below as well as compositions containing them. The norpsilocin compounds according to the disclosure, and the methods used to characterize them are described below.

Norpsilocin freebase is a compound of formula (I):

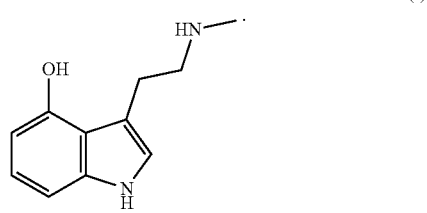

Norpsilocin fumarate is a compound of formula (II):

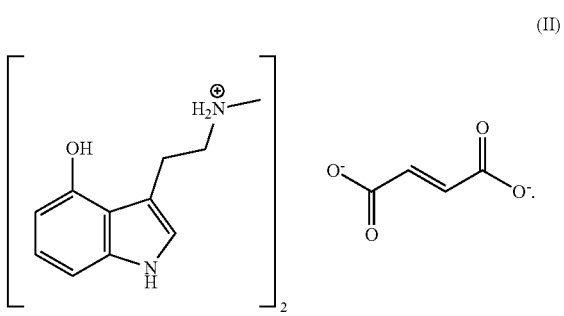

Methods of Treatment and Therapeutic Uses

In one embodiment, crystalline norpsilocin freebase, crystalline norpsilocin fumarate, or norpsilocin fumarate, according to the disclosure, and the methods and the compositions—particularly the pharmaceutical compositions—of the disclosure are used to regulate the activity of a neurotransmitter receptor by administering a therapeutically effective dose of crystalline norpsilocin freebase, crystalline norpsilocin fumarate, or norpsilocin fumarate of the disclosure. In another embodiment, crystalline norpsilocin freebase, crystalline norpsilocin fumarate, or norpsilocin fumarate, according to the disclosure, and the methods and the compositions—particularly the pharmaceutical compositions—of the disclosure are used to treat inflammation and/or pain by administering a therapeutically effective dose of crystalline norpsilocin freebase, crystalline norpsilocin fumarate, or norpsilocin fumarate of the disclosure.

Methods of the disclosure administer a therapeutically effective amount of crystalline norpsilocin freebase, crystalline norpsilocin fumarate, or norpsilocin fumarate of the disclosure to prevent or treat a disease or condition, such as those discussed below. Crystalline norpsilocin freebase, crystalline norpsilocin fumarate, or norpsilocin fumarate may be administered neat or as a pharmaceutical composition comprising crystalline norpsilocin freebase, crystalline norpsilocin fumarate, or norpsilocin fumarate as discussed below.

Crystalline norpsilocin freebase, crystalline norpsilocin fumarate, or norpsilocin fumarate, according to the disclosure may be used to prevent and/or treat a psychological disorder. The disclosure provides a method for preventing and/or treating a psychological disorder by administering to a subject in need thereof a therapeutically effective amount of crystalline norpsilocin freebase, crystalline norpsilocin fumarate, or norpsilocin fumarate of the disclosure, including the preferred embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Crystalline norpsilocin freebase, crystalline norpsilocin fumarate, or norpsilocin fumarate according to the disclosure may be used to prevent and/or treat a brain disorder. The disclosure provides a method for preventing and/or treating a brain disorder by administering to a subject in need thereof a therapeutically effective amount of crystalline norpsilocin freebase, crystalline norpsilocin fumarate, or norpsilocin fumarate of the disclosure, including the preferred embodiments discussed herein. The brain disorder may be chosen from Huntington's disease, Alzheimer's disease, dementia, and Parkinson's disease.

Crystalline norpsilocin freebase, crystalline norpsilocin fumarate, or norpsilocin fumarate according to the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline norpsilocin freebase, crystalline norpsilocin fumarate, or norpsilocin fumarate of the disclosure, including the preferred embodiments discussed herein.

Crystalline norpsilocin freebase, crystalline norpsilocin fumarate, or norpsilocin fumarate according to the disclosure may be used to prevent and/or treat inflammation and/or pain, such as, for example, inflammation and/or pain associated with inflammatory skeletal or muscular diseases or conditions. Accordingly, the disclosure relates to a method for preventing and/or treating inflammation and/or pain by administering to a subject in need thereof a therapeutically effective amount of crystalline norpsilocin freebase, crystalline norpsilocin fumarate, or norpsilocin fumarate of the disclosure, including the preferred embodiments discussed herein. Generally speaking treatable "pain" includes nociceptive, neuropathic, and mix-type. A method of the disclosure may reduce or alleviate the symptoms associated with inflammation, including, but not limited to, treating localized manifestation of inflammation characterized by acute or chronic swelling, pain, redness, increased temperature, or loss of function in some cases. A method of the disclosure may reduce or alleviate the symptoms of pain regardless of the cause of the pain, including, but not limited to, reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include, but are not limited to, musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compositions

The disclosure also relates to compositions comprising an effective amount of crystalline norpsilocin freebase, crystalline norpsilocin fumarate, or norpsilocin fumarate of the disclosure, including its preferred embodiments discussed above, and an excipient. In another embodiment of the disclosure, the disclosure also relates to pharmaceutical compositions comprising a therapeutically effective amount of crystalline norpsilocin freebase, crystalline norpsilocin fumarate, or norpsilocin fumarate of the disclosure, including its preferred embodiments discussed above, and a pharmaceutically acceptable excipient (also known as a pharmaceutically acceptable carrier). As discussed above, crystalline norpsilocin freebase, crystalline norpsilocin fumarate, or norpsilocin fumarate according to the disclosure may be, for example, therapeutically useful to prevent and/or treat the psychological disorders, brain disorders, pain and inflammation as well as the other disorders discussed above.

A composition or a pharmaceutical composition of the disclosure may be in any form which contains crystalline norpsilocin freebase, crystalline norpsilocin fumarate, or norpsilocin fumarate of the disclosure. The composition may be, for example, a tablet, capsule, liquid suspension, injectable, topical, or transdermal. The compositions generally contain, for example, about 1% to about 99% by weight of crystalline norpsilocin freebase, crystalline norpsilocin fumarate, or norpsilocin fumarate and, for example, 99% to 1% by weight of at least one suitable pharmaceutically acceptable excipient. In one embodiment, the composition may be between about 5% and about 75% by weight of crystalline norpsilocin freebase, crystalline norpsilocin fumarate, or norpsilocin fumarate with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline norpsilocin freebase, crystalline norpsilocin fumarate, or norpsilocin fumarate of the disclosure may be used as the "first purified psilocybin derivative" in the compositions described in US 2018/0221396 A1 and US 2019/0142851 A1. Accordingly, this disclosure provides a composition comprising as a first component: crystalline norpsilocin freebase, crystalline norpsilocin fumarate, or norpsilocin fumarate of the disclosure; and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutically effective amounts or by combination in a therapeutically effective amount to treat a disease, disorder, or condition as described herein. A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments.

A pharmaceutical formulation of the disclosure may comprise, consist essentially of, or consist of (a) crystalline norpsilocin freebase, crystalline norpsilocin fumarate, or norpsilocin fumarate and (b) a second active compound selected from a serotonergic drug, a purified psilocybin derivative, a purified cannabinoid, or a purified terpene and (c) a pharmaceutically acceptable excipient. Crystalline norpsilocin freebase, crystalline norpsilocin fumarate, or norpsilocin fumarate and the second active compound are each present in a therapeutically effective amount using a purposefully engineered and unnaturally occurring molar ratios. Exemplary molar ratios of crystalline norpsilocin freebase, crystalline norpsilocin fumarate, or norpsilocin fumarate to the second active compound in a composition of the disclosure include but are not limited to from about 0.1:100 to about 100:01, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing crystalline norpsilocin freebase, crystalline norpsilocin fumarate, or norpsilocin fumarate as discussed above may be used in place of a "purified psilocybin derivative" in the compositions described in US 2018/0221396 A1 and US 2019/0142851 A1. Accordingly, the disclosure provides a pharmaceutical formulation comprising as (a) crystalline norpsilocin freebase, crystalline norpsilocin fumarate, or norpsilocin fumarate and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Some exemplary serotonergic drugs include the following molecules: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds See Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In a preferred embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (Δ8-THC), Delta-8-tetrahydrocannabinolic acid (Δ8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed preferred embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

Exemplary compositions of crystalline norpsilocin freebase, crystalline norpsilocin fumarate, or norpsilocin fumarate and a second compound selected from a serotonergic drug, a purified psilocybin derivative, a purified cannabinoid, or a purified terpene in exemplary molar ratios are shown in Table 1.

TABLE 1

| Second Compound | Molar ratio of crystalline norpsilocin freebase, crystalline norpsilocin fumarate, or norpsilocin fumarate: second compound | Molar ratio of crystalline norpsilocin freebase, crystalline norpsilocin fumarate, or norpsilocin fumarate: second compound | Molar ratio of crystalline norpsilocin freebase, crystalline norpsilocin fumarate, or norpsilocin fumarate: second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

Exemplary pharmaceutical compositions of crystalline norpsilocin freebase, crystalline norpsilocin fumarate, or norpsilocin fumarate and a second compound selected from a serotonergic drug, a purified psilocybin derivative, a purified cannabinoid, or a purified terpene and an excipient with exemplary molar ratios of crystalline norpsilocin freebase, crystalline norpsilocin fumarate, or norpsilocin fumarate to the second compound are shown in Table 2.

TABLE 2

| Second Compound | Molar ratio of crystalline norpsilocin freebase, crystalline norpsilocin fumarate, or norpsilocin fumarate: second compound | Molar ratio of crystalline norpsilocin freebase, crystalline norpsilocin fumarate, or norpsilocin fumarate: second compound | Molar ratio of crystalline norpsilocin freebase, crystalline norpsilocin fumarate, or norpsilocin fumarate: second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

An "effective amount" or a "therapeutically effective amount" of crystalline norpsilocin freebase, crystalline norpsilocin fumarate, or norpsilocin fumarate of the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Crystalline norpsilocin freebase, crystalline norpsilocin fumarate, or norpsilocin fumarate of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter crystalline norpsilocin freebase, crystalline norpsilocin fumarate, or norpsilocin fumarate, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, crystalline norpsilocin freebase, crystalline norpsilocin fumarate, or norpsilocin fumarate may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of crystalline norpsilocin freebase, crystalline norpsilocin fumarate, or norpsilocin fumarate of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of crystalline norpsilocin freebase and crystalline norpsilocin fumarate are discussed below.

Preparation of Crystalline Norpsilocin Freebase and Crystalline Norpsilocin Fumarate Single crystals of norpsilocin freebase suitable for X-ray analysis were obtained from the slow evaporation of an acetone solution of a commercial sample of 4-hydroxy-N-methyltryptamine (Angene).

The norpsilocin fumarate was synthesized by starting with 101 mg of 4-hydroxy-N-methyltryptamine which was dissolved in 10 mL of methanol. 62 mg of fumaric acid was added to the solution and it was stirred overnight under reflux. The solvent was removed in vacuo to yield a dark blue powder. The powder was triturated with diethyl ether and then recrystallized in acetone to yield colorless crystals suitable for X-ray analysis.

$^1$H NMR (400 MHz, D$_2$O): δ 7.12 (s, 1H, ArH), 7.10-7.07 (m, 2H, ArH), 6.66 (s, 2H, CH), 6.56 (dd, J=5.5, 2.8 Hz, 1H, ArH), 3.41 (t, J=6.8 Hz, 2H, CH$_2$), 3.26 (t, J=6.8 Hz, CH$_2$), 2.70 (s, 3H, CH$_3$).

$^{13}$C NMR (100 MHz, D$_2$O): δ 171.0 (COOH), 149.7 (ArC), 138.5 (ArC), 134.2 (CH), 123.0 (ArC), 122.8 (ArC), 115.6 (ArC), 108.4 (ArC), 104.1 (ArC), 103.4 (ArC), 50.3 (CH$_2$), 32.4 (CH$_2$), 22.7 (CH$_3$).

Single crystal data, data collection and structure refinement details for crystalline norpsilocin freebase and crystalline norpsilocin fumarate are summarized in Table 3. The data for crystalline norpsilocin fumarate in Table 3 relates to the asymmetric unit.

TABLE 3

|  | Norpsilocin Freebase | Norpsilocin Fumarate |
|---|---|---|
| Chemical formula | C$_{11}$H$_{14}$N$_2$O | C$_{11}$H$_{15}$N$_2$O•C$_2$HO$_2$ |
| M$_r$ | 190.24 | 248.28 |
| Crystal system, space group | Monoclinic, P2$_1$/c | Triclinic, P$\bar{1}$ |
| Temperature (K) | 297 | 297 |
| a, b, c (Å) | 9.4060 (16), 8.8436 (15), 12.144 (2) | 7.7363 (10), 9.7146 (12), 9.7854 (13) |
| α (°) |  | 105.524 (4) |
| β (°) | 100.601 (7) | 110.554 (4) |
| γ (°) |  | 97.167 (4) |
| V (Å$^3$) | 993.0 (3) | 643.69 (14) |
| Z | 4 | 2 |
| Radiation type | Mo Kα | Mo Kα |
| μ (mm$^{-1}$) | 0.08 | 0.09 |
| Crystal size (mm) | 0.35 × 0.2 × 0.1 | 0.24 × 0.19 × 0.03 |
| F(000) | 408 | 264 |
| D$_x$ (Mg m$^{-3}$) | 1.273 | 1.281 |
| λ (Å) | 0.71073 | 0.71073 |
| θ (°) | 2.9-26.0 | 2.7-25.5 |
| BLOCK | Colourless | Colourless |
| Diffractometer | Bruker D8 Venture CMOS | Bruker D8 Venture CMOS |
| Absorption correction | Absorption correction: multi-scan SADABS2016/2 (Bruker, 2016/2) was used for absorption correction. wR2(int) was 0.0546 before and 0.0457 after correction. The Ratio of minimum to maximum transmission is 0.9612. The λ/2 correction factor is Not present. | Absorption correction: multi-scan SADABS2016/2 (Bruker, 2016/2) was used for absorption correction. wR2(int) was 0.0541 before and 0.0477 after correction. The Ratio of minimum to maximum transmission is 0.9187. The λ/2 correction factor is Not present. |
| T$_{min}$, T$_{max}$ | 0.716, 0.745 | 0.685, 0.745 |
| No. of measured, independent and observed [I > 2σ(I)] reflections | 35681, 1955, 1687 | 14395, 2365, 1774 |
| R$_{int}$ | 0.031 | 0.046 |
| θ$_{max}$, θ$_{min}$ (°) | 26.1, 3.2 | 25.5, 2.7 |
| h | −11→11 | −9→9 |
| k | −10→10 | −11→11 |
| l | −14→15 | −11→11 |
| Refinement | F$^2$ | F$^2$ |
| Least-squares matrix | Full | Full |
| R[F$^2$ > 2σ(F$^2$)], wR(F$^2$), S | 0.053, 0.146, 1.08 | 0.039, 0.098, 1.11 |
| No. of reflections | 1955 | 2365 |
| No. of parameters | 137 | 181 |
| No. of restraints | 3 | 4 |
| Hydrogen site location | Mixed | Mixed |
| H-atom treatment | H atoms treated by a mixture of independent and constrained refinement | H atoms treated by a mixture of independent and constrained refinement |

TABLE 3-continued

|  | Norpsilocin Freebase | Norpsilocin Fumarate |
|---|---|---|
| w | $1/[\sigma^2(F_o^2) + (0.0686P)^2 + 0.560P]$ where $P = (F_o^2 + 2F_c^2)/3$ | $1/[\sigma^2(F_o^2) + (0.0428P)^2 + 0.1031P]$ where $P = (F_o^2 + 2F_c^2)/3$ |
| $(\Delta/\sigma)_{max}$ | <0.001 | <0.001 |
| $\Delta\rho_{max}, \Delta\rho_{min}$ (e Å$^{-3}$) | 0.59, −0.22 | 0.15, −0.15 |
| Extinction Correction |  | SHELXL2018/3 (Sheldrick 2018), $Fc^* = kFc[1 + 0.001 \times Fc^2\lambda^3/\sin(2\theta)]^{-1/4}$ |
| Extinction Coefficient |  | 0.035 (8) |

Data collection: APEX3 (Bruker, 2018). Cell refinement: SAINT (Bruker, 2018) for umd2019e_a; SAINT (Bruker, 2018 for umd2025f_a. Data reduction: SAINT for umd2019e_a; SAINT (Bruker, 2018) for umd2025f_a. Program(s) used to solve structure: SHELXT2014 (Sheldrick 2015a); program(s) used to refine structure: SHELXL2018 (Sheldrick, 2015b); molecular graphics: OLEX2 (Dolomanov et al., 2009); software used to prepare material for publication: publCIF (Westrip, 2010).

The molecular structure of crystalline norpsilocin freebase is shown in FIG. 1. The asymmetric unit contains one full 4-hydroxy-N-methyltryptamine ($C_{11}H_{14}N_2O$) molecule. The indole ring system of the tryptamine is near planar with an r.m.s. deviation from planarity of 0.015 Å. The ethylamine arm of the tryptamine is slightly turned, with a C7-C8-C9-C10 torsion angle of 26.7 (3)°.

Figure 2:
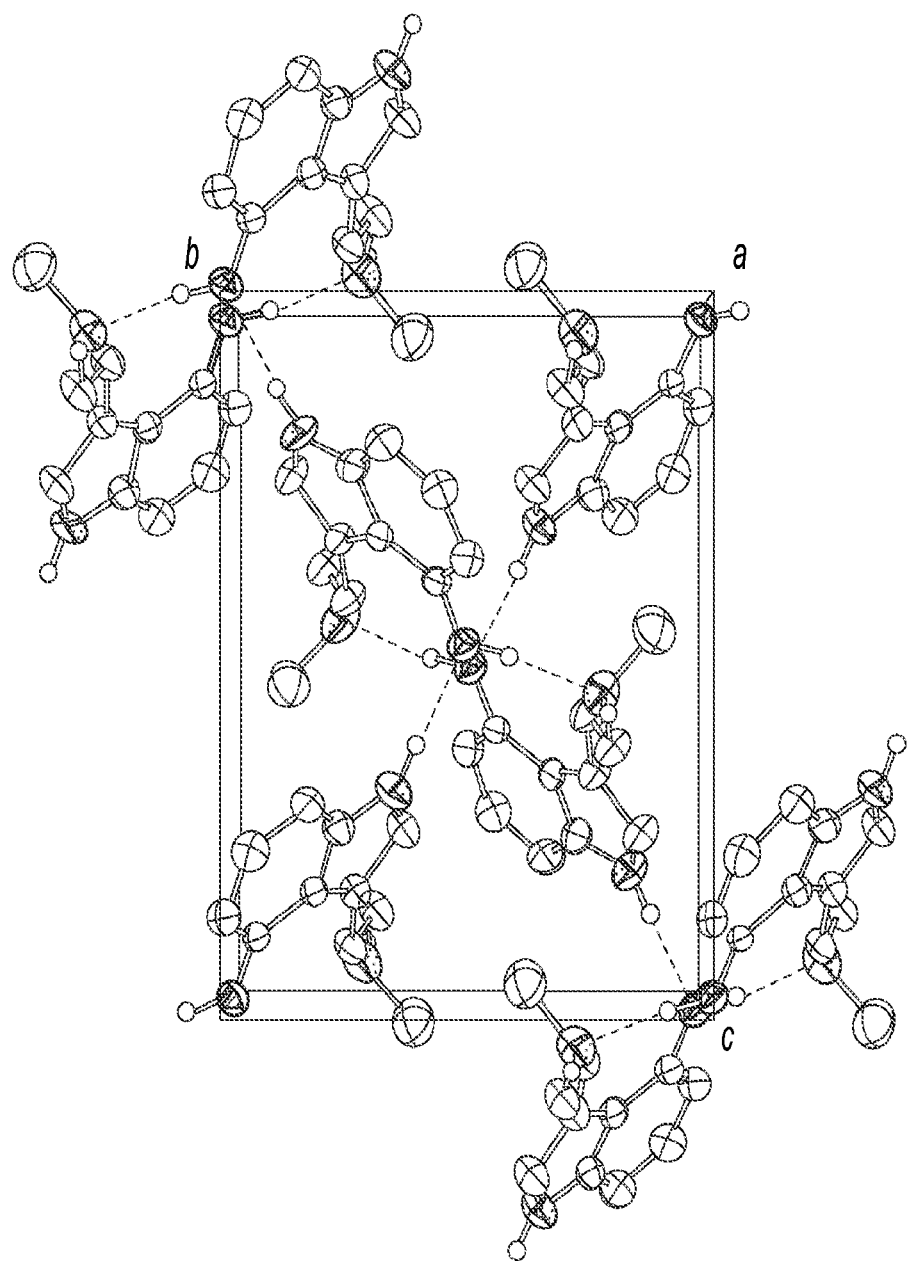
FIG. 2 shows the packing of crystalline norpsilocin freebase.

The tryptamine molecules of the norpsilocin freebase are held in an infinite two-dimensional network along the (100) plane through a series of N—H . . . O and O—H . . . N hydrogen bonds. The phenol O—H hydrogen bonds with the nitrogen of the methylamine of another tryptamine molecule. The indole N—H hydrogen bonds with the phenol oxygen of another tryptamine molecule. The packing of crystalline norpsilocin freebase is shown in FIG. 2.

Figure 3:
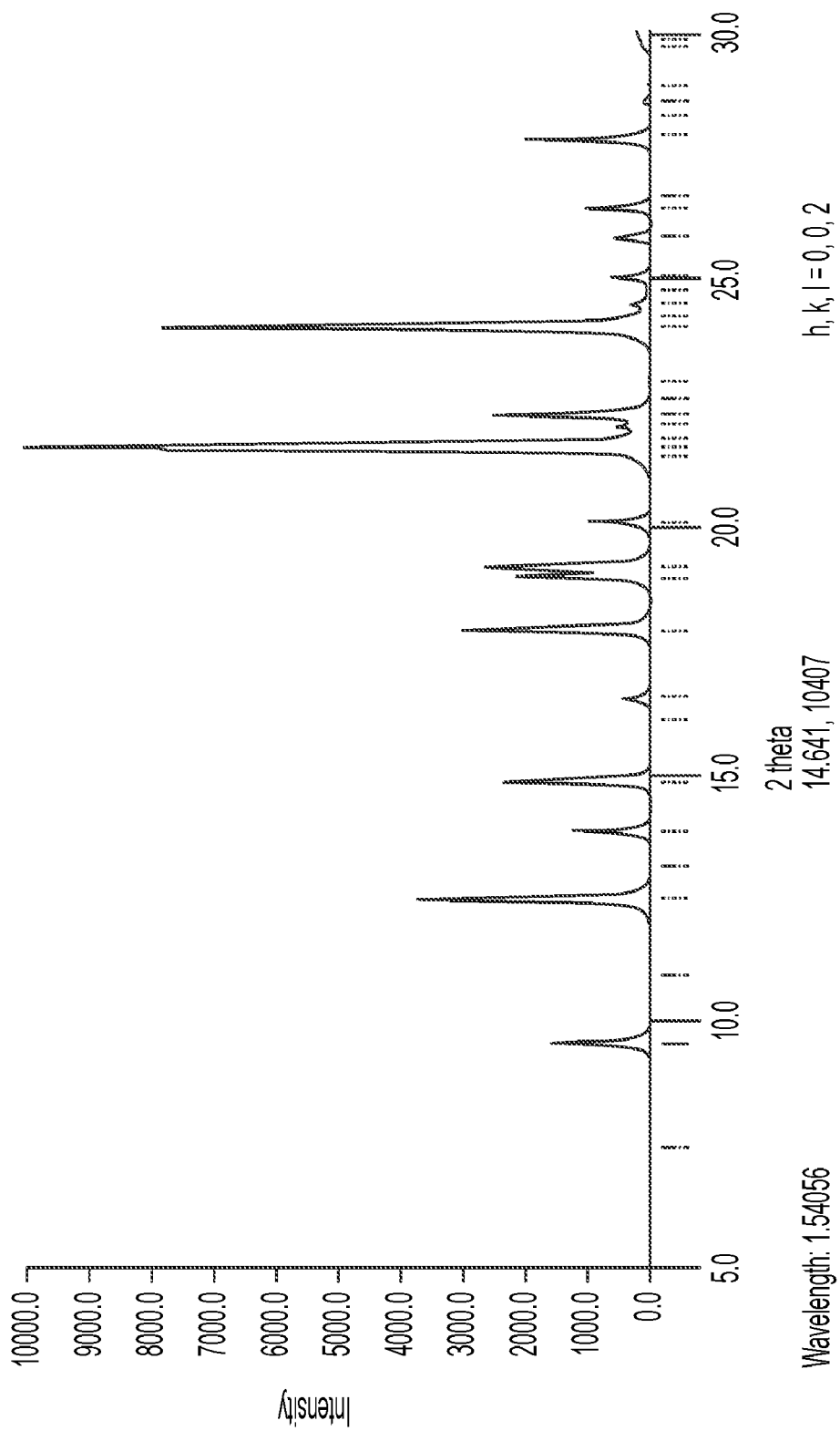
FIG. 3 shows a simulated x-ray power diffraction (XRPD) of crystalline norpsilocin freebase.

FIG. 3 is a simulated x-ray powder diffraction (XRPD) of crystalline norpsilocin freebase from its single crystal data. Crystalline norpsilocin freebase may be characterized by the XRPD peaks at 9.6, 12.4, and 17.9°2θ±0.2°2θ as well as by an XRPD pattern substantially similar to FIG. 3.

Figure 4:
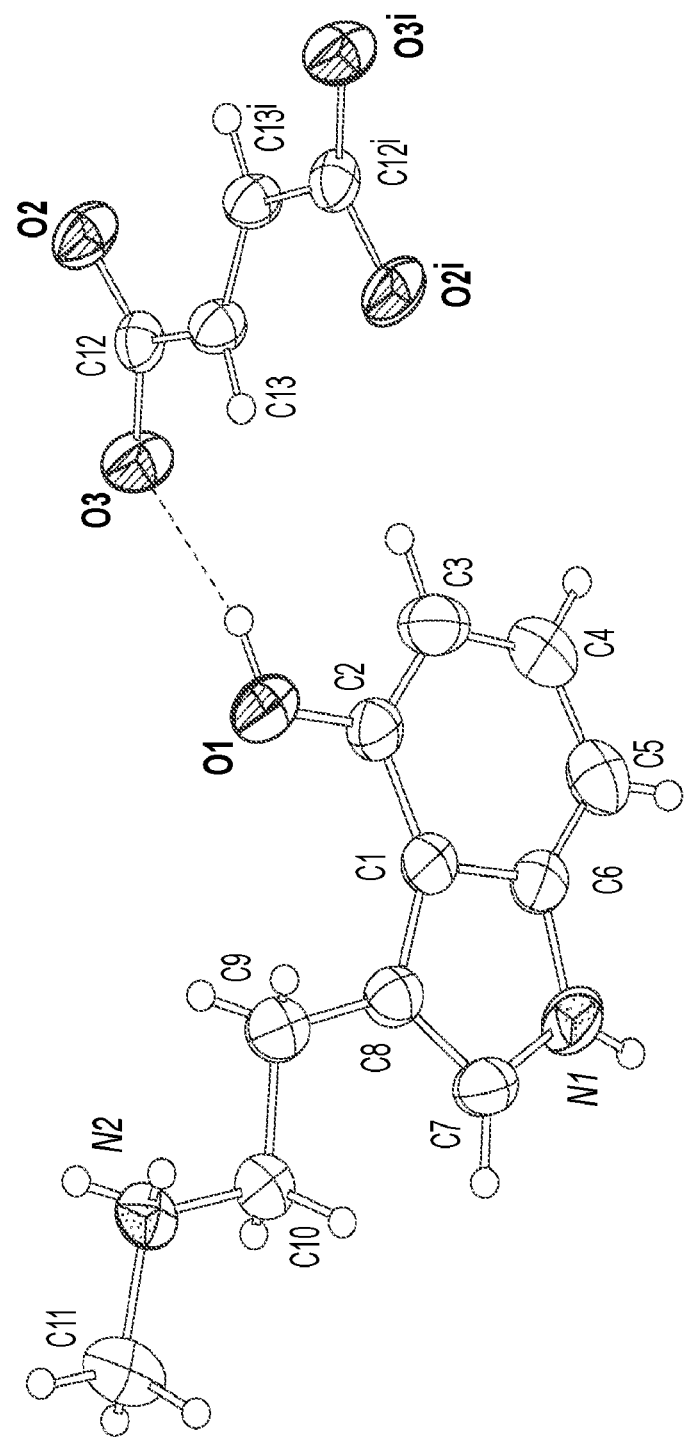
FIG. 4 shows the molecular structure of crystalline norpsilocin fumarate.

The molecular structure of crystalline norpsilocin fumarate is shown in FIG. 4. The asymmetric unit contains one full 4-hydroxy-N-methyltryptammonium ($C_{11}H_{15}N_2O^+$) cation and one half of a fumarate ($C_4H_2O_4^{2-}$) dianion. The indole ring system of the tryptamine is near planar with an r.m.s. deviation from planarity of 0.009 Å. Unlike norpsilocin freebase, the ethyl ammonium arm also stays in the same plane of the indole. The planarity of all of the nonhydrogen atoms of the tryptamine have an r.m.s. deviation from planarity of only 0.043 Å. The fumarate itself is also near planar, with an r.m.s. deviation from planarity of 0.050 Å.

Figure 5:
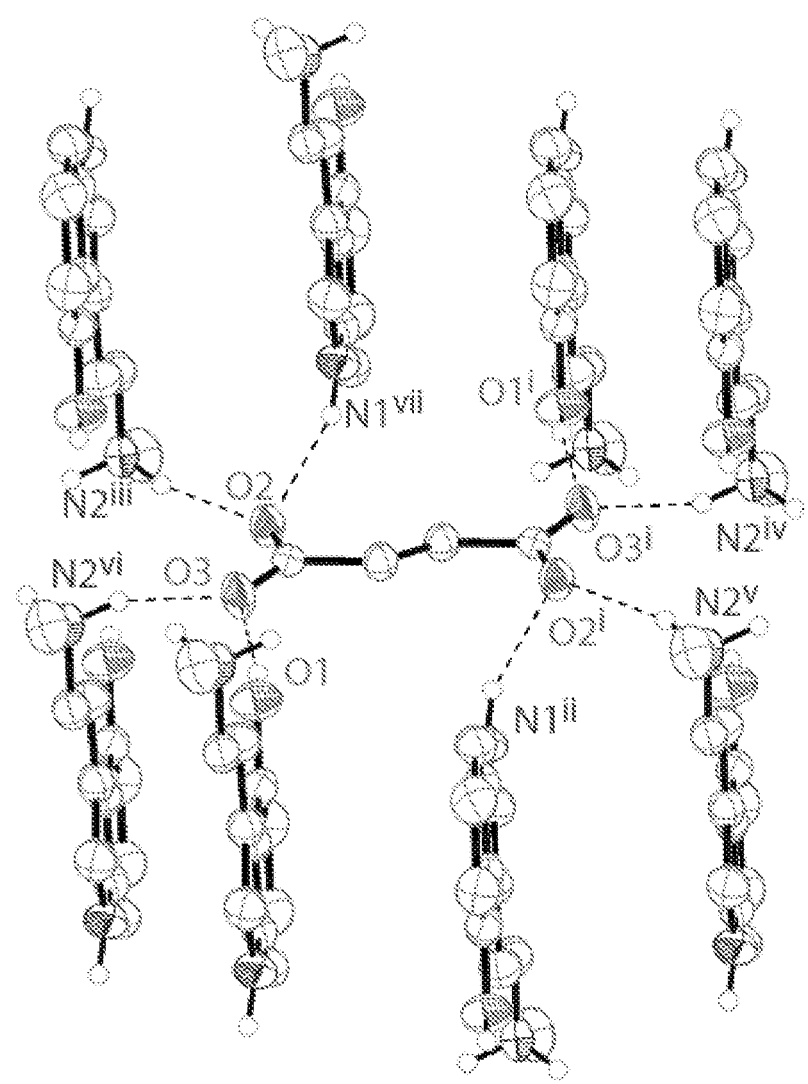
FIG. 5 shows the indole N—H, methylammonium N—H, and phenol O—H hydrogen bonds with the oxygen atoms of the norpsilocin fumarate dianion.
Figure 6:
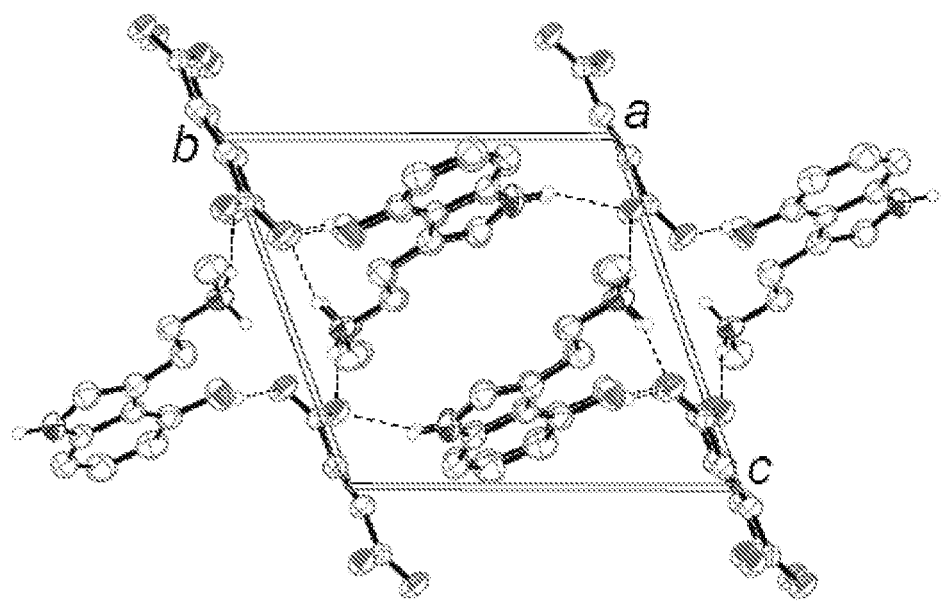
FIG. 6 shows the packing of crystalline norpsilocin fumarate.

The tryptammonium cations and the fumarate dianions of the norpsilocin fumarate are held together in an infinite three-dimensional framework through a series of N—H . . . O and O—H . . . O hydrogen bonds. The indole N—H, methylammonium N—H, and phenol O—H all hydrogen bond with the oxygen atoms of the fumarate dianion are shown in FIG. 5. The six-membered rings of the indoles stack with parallel slipped π-π interactions [intercentroid distance=3.6465 (15) Å, interplanar distance=3.4781 (16) Å, and slippage=1.095 (3) Å]. The packing of crystalline norpsilocin fumarate is shown in FIG. 6.

Figure 7:
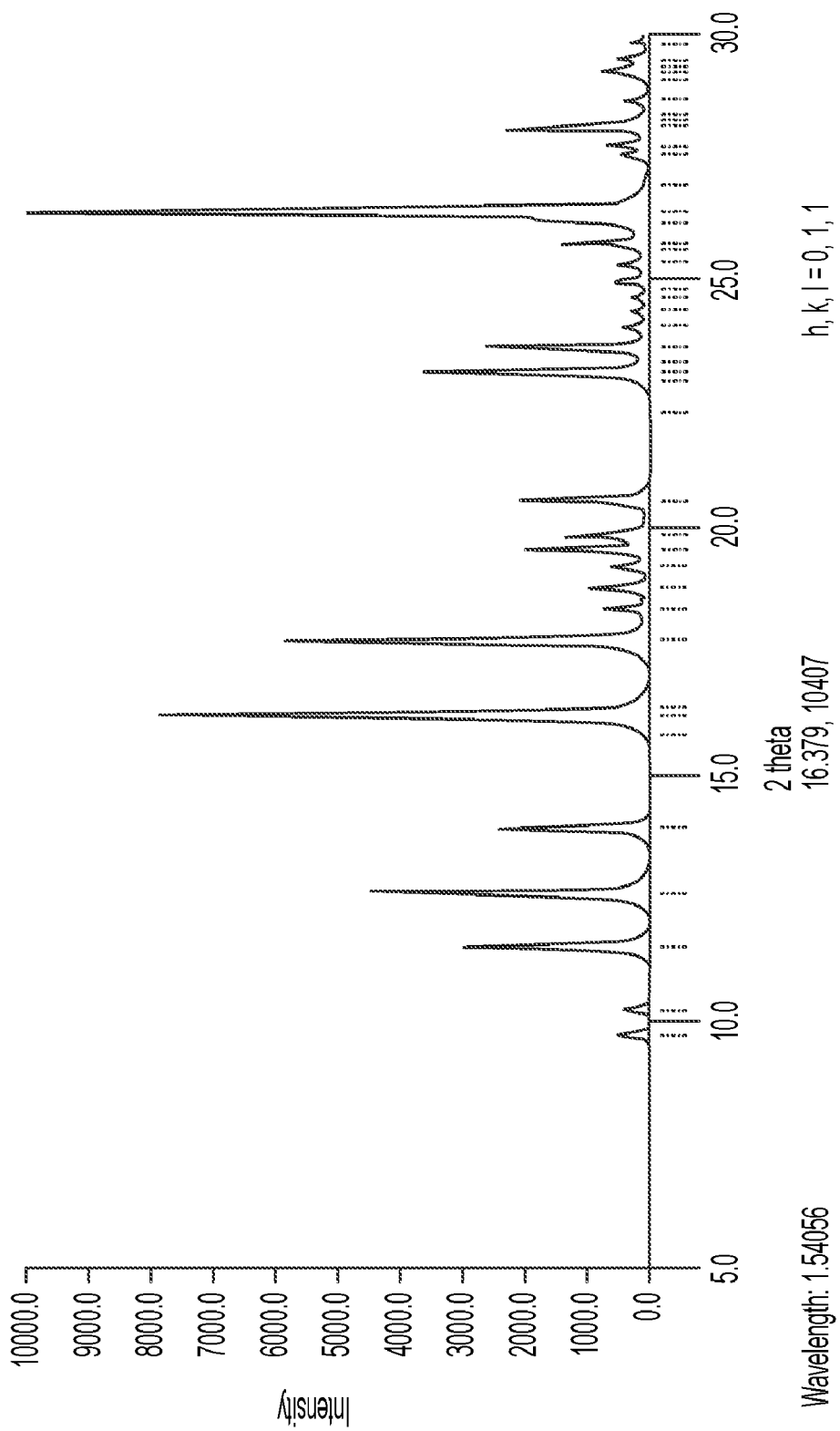
FIG. 7 shows a simulated x-ray power diffraction (XRPD) of crystalline norpsilocin fumarate.

FIG. 7 is a simulated x-ray powder diffraction (XRPD) of crystalline norpsilocin fumarate from its single crystal data. Crystalline norpsilocin fumarate may be characterized by the XRPD peaks at 11.5, 13.9, and 16.2°2θ±0.2°2θ as well as by an XRPD pattern substantially similar to FIG. 7.

REFERENCES

Aixalà, M., Dos Santos, R. G., Hallak, J. E. C. & Bouso, J. C. (2018). ACS Chem. Neurosci. 9, 2304-2306.

Bradley, R. J. & Johnston, V. S. (1970). Origin and Mechanism of Hallucinations, edited by W. Keup, pp. 333-344. New York: Plenum Press.

Bruker (2018). APEX3, SAINT, and SADABS. Bruker AXS Inc., Madison, Wisconsin, USA.

Cameron, L. P., Benson, C. J., DeFelice, B. C., Fiehn, O. & Olson, D. E. (2019). ACS Chem. Neurosci. In the press. http://doi.org/10.1021/acschemneuro.8b00692.

Cameron, L. P. & Olson, D. E. (2018). ACS Chem. Neurosci. 9, 2344-2357.

Carhart-Harris, R. L. & Goodwin, G. M. (2017). Neuropsychopharmacology, 42, 2105-2113.

Dinis-Oliveira, R. J. (2017). Drug Metab. Rev. 49, 84-91.

Dolomanov, O. V., Bourhis, L. J., Gildea, R. J., Howard, J. A. K. & Puschmann, H. (2009). J. Appl. Cryst. 42, 339-341.

Fontanilla, D., Johannessen, M., Hajipour, A. R., Cozzi, N. V., Jackson, M. B. & Ruoho, A. E. (2009). Science, 323, 934-937.

J. Gartz, Int. J. Crude Drug Res., 1989, 27, 141-144.

N. Jensen, J. Gartz and H. Laatsch, Planta Med., 2006, 72, 665-666.

Johnson, M. W. & Griffiths, R. R. (2017). Neurotherapeutics 14, 734-740.

Lenz, C., Wick, J. & Hoffmeister, D. (2017). J. Nat. Prod. 80, 2835-2838.

Leung, A. Y. & Paul, A. G. (1968). J. Pharm. Sci. 57, 1667-1671.

Nichols, D. E. (2012). WIREs Membr. Transp. Signal. 1, 559-579.

Nichols, D. E. (2016). Pharmacol. Rev. 68, 264-355.

Passie, T., Seifert, J., Schneider, U. & Emrich, H. M. (2002). Addict. Biol. 7, 357-364.

Russo, E. B. (2011). Br. J. Pharmacol. 163, 1344-1364.

Sheldrick, G. M. (2015a). Acta Cryst. A71, 3-8

Sheldrick, G. M. (2015b). Acta Cryst. C71, 3-8.

Sherwood, A. M., Halberstadt, A. L., Klein, A. K., McCorvy, J. D., Kaylo, K. W., Kargbo, R. B. & Meisenheimer, P. (2020). J. Nat. Prod. 83, 461-467.

Stamets, P. (1996). Psilocybin mushrooms of the world: An identification guide. Berkeley, CA: Ten Speed Press.

Westrip, S. P. (2010). J. Appl. Cryst. 43, 920-925.

Zhuk, O., Jasicka-Misiak, I., Poliwoda, A., Kazakova, A., Godovan, V. V., Halama, M. & Wieczorek, P. (2015). Toxins, 7, 1018-1029.

The claimed invention is:

1. A composition comprising crystalline 4-hydroxy-N-methyltryptammonium fumarate (norpsilocin fumarate) and an excipient, wherein crystalline norpsilocin fumarate is characterized by: a triclinic, P1̄ crystal system space group at a temperature of about 297 K;

unit cell dimensions a=7.7363 (10) Å, b=9.7146 (12) Å, c=9.7854 (13) Å, α=105.524 (4)°, β=110.554 (4)°, and γ=97.167 (4)°;

an XRPD having peaks at 11.5, 13.9, and 16.2°2θ±0.2° 2θ; or an XRPD pattern substantially similar to FIG. 7.

2. A composition comprising crystalline 4-hydroxy-N-methyltryptammonium fumarate (norpsilocin fumarate) and a second component selected from (a) a serotonergic drug, (b) a purified psilocybin derivative, (c) one or two purified cannabinoids and (d) a purified terpene, wherein crystalline norpsilocin fumarate is characterized by:

a triclinic, $P\bar{1}$ crystal system space group at a temperature of about 297 K;

unit cell dimensions a=7.7363 (10) Å, b=9.7146 (12) Å, c=9.7854 (13) Å, α=105.524 (4)°, β=110.554 (4)°, and γ=97.167 (4)°;

an XRPD having peaks at 11.5, 13.9, and 16.2°2θ±0.2° 2θ; or an XRPD pattern substantially similar to FIG. 7.

3. 4-hydroxy-N-methyltryptammonium fumarate (norpsilocin fumarate).

4. A composition comprising 4-hydroxy-N-methyltryptammonium fumarate (norpsilocin fumarate) according to claim 3 and an excipient.

5. A composition comprising 4-hydroxy-N-methyltryptammonium fumarate (norpsilocin fumarate) according to claim 3 and a second component selected from (a) a serotonergic drug, (b) a purified psilocybin derivative, (c) one or two purified cannabinoids and (d) a purified terpene.

6. A method of treating a psychological disorder comprising the step of:

administering to a subject in need thereof a therapeutically effective amount of 4-hydroxy-N-methyltryptammonium fumarate (norpsilocin fumarate) according to claim 3.

7. A method of treating a psychological disorder comprising the step of:

administering to a subject in need thereof a composition according to claim 4.

8. A method of treating inflammation and/or pain comprising the step of:

administering to a subject in need thereof a therapeutically effective amount of 4-hydroxy-N-methyltryptammonium fumarate (norpsilocin fumarate) according to claim 3.

9. A method of treating inflammation and/or pain comprising the step of:

administering to a subject in need thereof a composition according to claim 4.

10. A method of treating a psychological disorder comprising the step of:

administering to a subject in need thereof a composition according to claim 5.

11. A method of treating inflammation and/or pain comprising the step of:

administering to a subject in need thereof a composition according to claim 5.

* * * * *